(12) United States Patent
Zhang et al.

(10) Patent No.: US 8,578,754 B2
(45) Date of Patent: Nov. 12, 2013

(54) ADSORBED GAS CONTENT MEASURING INSTRUMENT AND ITS TESTING METHOD

(76) Inventors: Jinchuan Zhang, Beijing (CN); Ying Tang, Beijing (CN); Xuan Tang, Beijing (CN); Zhonglin Song, Beijing (CN); Dejian Zhai, Beijing (CN); Hui Xue, Beijing (CN)

(*) Notice: Subject to any disclaimer, the term of this patent is extended or adjusted under 35 U.S.C. 154(b) by 385 days.

(21) Appl. No.: 13/010,795

(22) Filed: Jan. 21, 2011

(65) Prior Publication Data

US 2011/0239732 A1 Oct. 6, 2011

(30) Foreign Application Priority Data

Apr. 1, 2010 (CN) .......................... 2010 1 0137275

(51) Int. Cl.
*G01N 33/18* (2006.01)
*G01N 1/22* (2006.01)
*G01N 1/12* (2006.01)

(52) U.S. Cl.
USPC ...................... 73/19.1; 73/863.12; 73/864.63

(58) Field of Classification Search
USPC ........ 73/19.01, 19.1, 863.11, 863.12, 864.51, 73/864.63; 95/241, 250, 251, 254, 257
See application file for complete search history.

(56) References Cited

U.S. PATENT DOCUMENTS

| 4,089,206 | A | * | 5/1978 | Raffel et al. | ................... | 73/19.1 |
| 4,325,247 | A | * | 4/1982 | Foss | ............................... | 73/19.1 |
| 6,740,294 | B2 | * | 5/2004 | Radmacher et al. | ............ | 422/83 |

* cited by examiner

*Primary Examiner* — Hezron E Williams
*Assistant Examiner* — Nathaniel Kolb

(57) ABSTRACT

The present invention relates to an adsorbed gas content measuring instrument and its testing method. The instrument comprises sealed cylinders, gas collecting graduated canisters and a test box, wherein the sealed cylinders are provided with valves, the gas collecting graduated canisters are equipped with drain hole adjustment valves and vent hole switching valves fit for the valve ports, and there is a heating element and a temperature controller in the test box. The method is mainly as follows: put gas-contained samples and saturated brine into the sealed cylinder, seal the cylinder, feed water in the test box and heat the box, place the sealed cylinder into the water bath of the test box, introduce saturated brine into the gas collecting graduated canister, connect the canister and cylinder, open the drain hole of the gas collecting graduated canister, record the liquid level of the graduated canister and cut off the connection after the test. The present invention has a compact structure, small volume, good gas tightness, accurate measurement, uniform heating and simple testing operation, is easy to move and carry, and suitable for field application. It can be specially used for collecting and measuring various gases, especially small-volume gas, thus it is more practical in applications.

10 Claims, 3 Drawing Sheets

ADSORBED GAS CONTENT MEASURING INSTRUMENT AND ITS TESTING METHOD

BACKGROUND OF THE INVENTION

The present invention relates to a gas analysis testing equipment and its testing method, and more especially, to an adsorbed gas content measuring instrument and its testing method.

Adsorbed gas means natural gas existent in gaps and cracks in a reservoir bed. In a normal natural gas reservoir bed, the adsorbed gas content is low, generally less than 20%; in an unconventional natural gas reservoir bed, the adsorbed gas content is high, the adsorbed gas contained in natural gas of a coal-seam gas reservoir bed is generally more than 85%, the adsorbed gas contained in natural gas of a shale gas reservoir bed is 20-85%. The content of adsorbed gas directly concerns the quality of the natural gas aggregates and the technology required during development. Especially, for normal natural gas such as coal-seam gas and shale gas, the adsorbed gas content is the key factor of reservoir bed evaluation, reservoir calculation, development and design. Therefore, the test of natural gas adsorbed gas content in gas contained sample has been widely applied in natural gas exploration and development, and has become an important aspect in natural gas resource development. Moreover, it is also broadly applied in metal mine exploitation, gas explosion prevention, environmental protection and monitoring, pedologic research, chemical industry and other fields.

There has been no testing equipment that is special for accurately measuring the adsorbed gas content at present. When the adsorbed gas content is tested by conventional testing equipment, it is required to place the gas contained sample in the sealed cylinder for analysis reaction, one end of the gas duct is connected with the interior of the puncture pinhead, the other end extends into the opening of the burette which is placed below the water tank liquid level with the opening downwards and bottom communicating with the gas collecting duct. Spring clamps or screw clamps can be set on the gas duct and gas collecting duct as desired.

The testing system assembled according to the abovementioned conventional lab equipment can basically meet the requirements of the natural gas for analysis reaction, collection and content measurement. However, in real-life application, we find that the testing system has the following defects:

1. Several segments of gas duct in corresponding length are required for the test; the duct must be filled up with air; when the air content is very low during analysis, the measuring result of the content of the analyzed gas collected by means of the existing testing system is very likely to be zero or has high deviation from the actual result; meanwhile, the air residue in the sealed cylinder is impossible to be emptied; fresh air is prone to be mixed during collection of analyzed gas; the testing system has a highly exposed area and is highly affected by the environment. Therefore, the testing accuracy is too inferior to meet the requirement for accurate measurement;

2. A long preparation time for the test is required and the operation process is complicated, so it is inconvenient for simultaneous execution and unsatisfactory for real-life needs;

3. In the test, it is required to test the sample to the initial temperature, but the existing testing system is incapable of accurately and stably controlling the corresponding testing temperature;

4. The equipment has high volume and is made of glass containers mainly, bearing less safety and stability. If carrying it to the site for testing, there are a lot of difficulties such as high volume, heavy height, proneness to be broken and damaged;

Therefore, the abovementioned equipment for measuring the adsorbed gas content and its testing method are to be further improved due to the inconvenience and defect in structure and usage. One of the key research subjects in this field is how to create a new adsorbed gas content measuring instrument with a compact structure, small volume, good gas tightness, accurate measurement, uniform heating and convenient & simple & rapid operation, easy to move and carry and suitable for field application, special for measuring and collecting various gases such as natural gas, especially small volume gases.

BRIEF SUMMARY OF THE INVENTION

The technical problem to be solved by the present invention is to provide an adsorbed gas content measuring instrument which is with a compact structure, small volume, good gas tightness, accurate measurement, uniform heating and convenient & simple & rapid operation, easy to move and carry and suitable for field application, special for measuring and collecting various gases of small volume gases, so as to overcome the deficiency of the adsorbed gas content measuring instrument in the prior art.

To address the abovementioned technical problem, an adsorbed gas content measuring instrument is disclosed by the present invention, which mainly comprises sealed cylinders, gas collecting graduated canisters and a test box, wherein the sealed cylinder includes a cylinder body, a top cover fixedly connected with one end of the cylinder body, a bottom cover removably connected with the other end of the cylinder body and a valve port fixed on the top cover; the gas collecting graduated canister includes a sealed canister body with scale marks, a seal with a drain hole and a vent hole, wherein the drain hole is provided with an adjustment valve, the vent hole is equipped with a switching valve fit for the valve port of the sealed cylinder; a heating element, a temperature controller for monitoring the temperature inside the box and a top plate are fixed in the test box; there are several through holes with diameter corresponding to the outer diameter of the sealed cylinders and gas collecting graduated canisters on the top plate; the sealed cylinders and gas collecting graduated canisters are placed in the corresponding through holes; the heating element and the temperature controller are connected with the power interface outside the box.

As an improvement of the present invention, the valve port of the sealed cylinder is the male buckle of the rapid connection buckle, the switching valve of the gas collecting graduated canister is the female buckle fit for the male buckle.

The adjustment valve of the gas collecting graduated canister is composed of a restriction disk, an adjustment handwheel and adjustment screws, wherein the restriction disk is located inside the seal, and restriction orifices are arranged with diameters increasing along the circumference; the adjustment handwheel is located outside the seal, through holes corresponding to the quantity and position of the restriction orifices are configured, and the diameters of the through holes are similar to those of the maximum restriction orifices; the position and size of the vent hole on the seal of the gas collecting graduated canister is similar to that of a through hole on the adjustment handwheel; the restriction disk and adjustment handwheel are connected via the adjustment screws and rotate synchronously.

The middle part of the top cover of the sealed cylinder has a rising; between the middle part and the outer edge of the top cover is an inclined surface.

A boss is set on the bottom cover of the cylinder towards one side of the interior of the cylinder.

The text box further includes a cover, a drain valve, partitioning plate and adhesion plate, wherein: the cover is above the test box; the drain valve is mounted at the bottom of the test box; the drain valve is mounted at the bottom of the test box; the heating element is fixed on the inner wall of the box bottom, the partitioning plate is fixed above the heating element and several through holes are set; holes corresponding to the top plate are set on the adhesion plate and installed in the middle of the test box removably.

The cylinder body of the sealed cylinder is buckled with the bottom cover.

It further comprises a bracket for supporting and stabilizing the gas collecting graduated canisters.

In addition, the present invention further provides a testing method of the said adsorbed gas content measuring instrument, comprising the following steps: A. take out the sealed cylinders and the gas collecting graduated canisters; B. open the bottom cover of the sealed cylinder, introduce gas contained sample, fill up with saturated brine and then seal the cylinder; C. feed water in the text box, turn the switch on, heat the water to the required temperature by means of the temperature controller and the heating element, and place the sealed cylinder into the text box vertically with the top cover upwards; D. fill the gas collecting graduated canister up with the saturated brine; E. connect the sealed cylinder and the gas collecting graduated canister with the seal downwards, and open the drain holes of the gas collecting graduated canister; F. record the liquid level of the gas collecting graduated canister regularly; G. after test, close the drain holes of the gas collecting graduated canister, and disconnect the connection it from the sealed cylinder.

The following steps are further included between Step A and B: feed the saturated brine into the gas collecting graduated canisters, vertically place them with the seal downwards, adjust the adjustment valves, select the maximum opening size capable of preventing the brine from leaking as the opening size of the drain holes in Step E, afterwards, close the drain holes for the next use.

With such design, the adsorbed gas content measuring instrument for the present invention is with a compact structure, small volume, good gas tightness, accurate measurement, simple & rapid operation and uniform heating, easy to move and carry, and suitable for field application. It can be specially used for collecting and measuring various gases, especially small-volume gas, thus it is more practical in applications.

BRIEF DESCRIPTION OF THE DRAWINGS

The description above is only a brief introduction of the technical solution of the present invention. To more clearly understand the technician means, the present invention is further detailed in combination with the drawings and the embodiments.

DETAILED DESCRIPTION OF THE INVENTION

Figure 1:
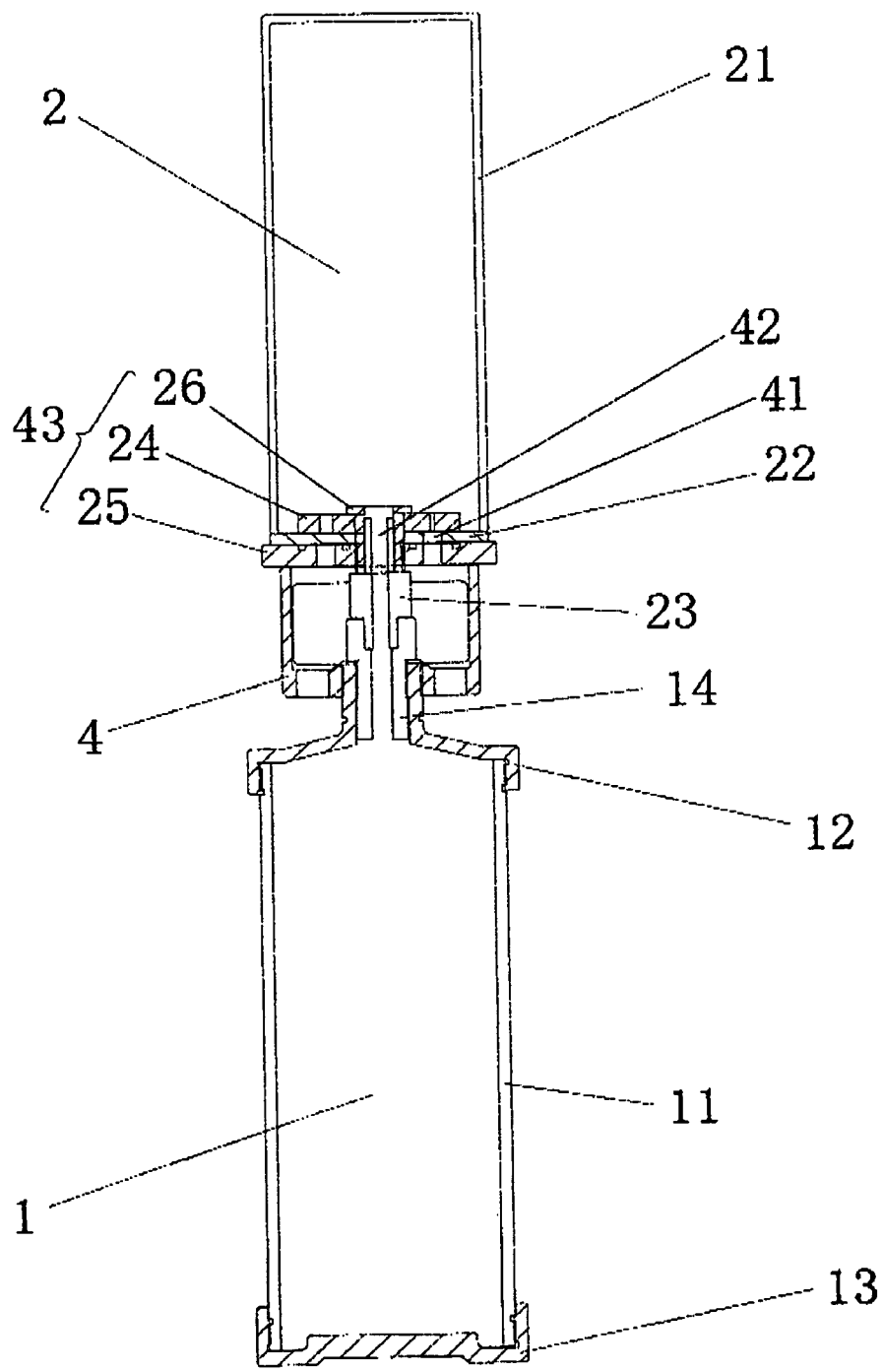
FIG. 1 is the schematic view of the assembly structure of the sealed cylinders and gas collecting graduated canisters for the present adsorbed gas content measuring instrument.

As shown in FIG. 1-4, the adsorbed gas content measuring instrument for the present invention mainly comprises sealed cylinders 1, gas collecting graduated canisters 2 and a test box 3, wherein, the sealed cylinder 1 includes a cylinder body 11, a top cover 12 fixedly connected with one end of the cylinder body, a bottom cover 13 removably connected with the other end of the cylinder body and a valve port 14 fixed on the top cover.

Preferably, the valve port 14 adopts the male buckle of the rapid connection buckle, such as rapid connection produced by Colder Products Company of the US. The middle part of the top cover 12 of the sealed cylinder has a rising, and between the middle part and the outer edge of the top cover is an inclined surface, so as to collect gas when the volume is very small. The cylinder body 11 is buckled with the bottom cover 13 for the purpose of improving operation efficiency and avoiding gas spreading. A boss is set on the bottom cover 13 towards one side of the interior of the cylinder body so as to empty the air in the cylinder when buckling.

The gas collecting graduated canister 2 includes a sealed canister body 21 with scale marks, a seal 22 with a drain hole 41 and a vent hole 42, wherein the drain hole is provided with adjustment valve 43, the vent hole is equipped with switching valve 23 fit for the valve port 14 of the sealed cylinder.

Figure 2:
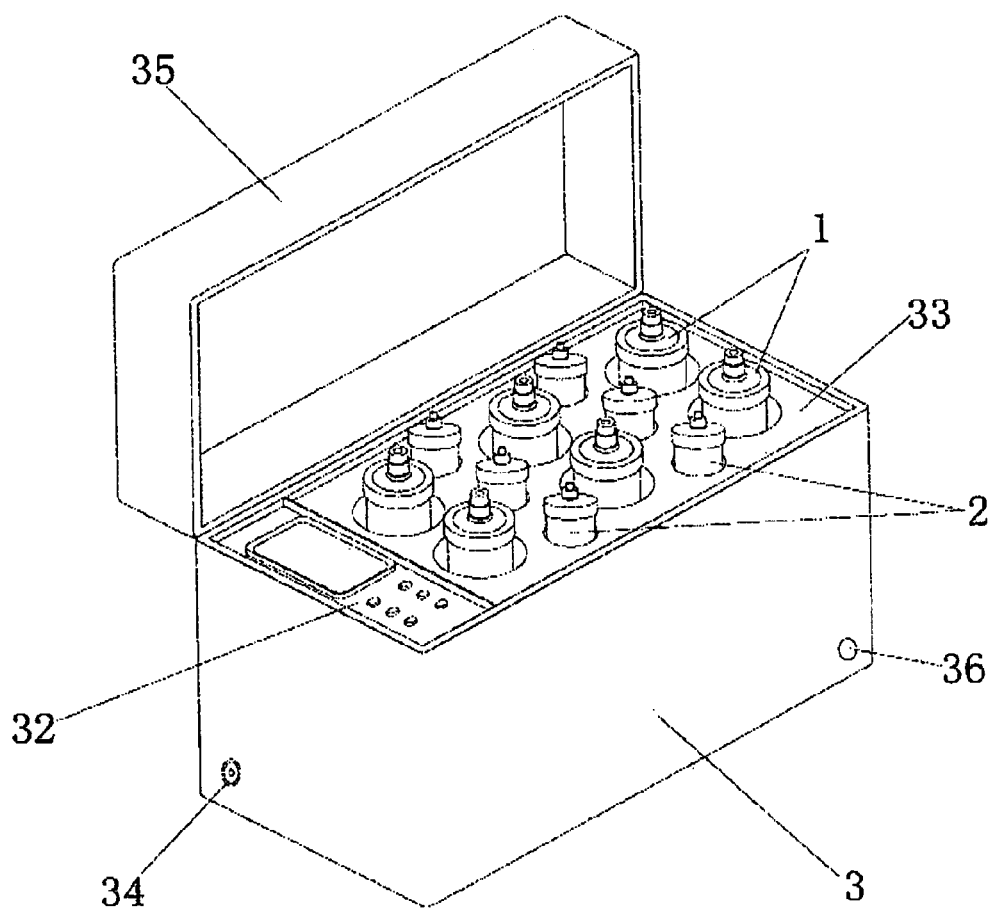
FIG. 2 is the schematic view of the restriction disk of the gas collecting graduated canisters for the present adsorbed gas content measuring instrument.
Figure 3:
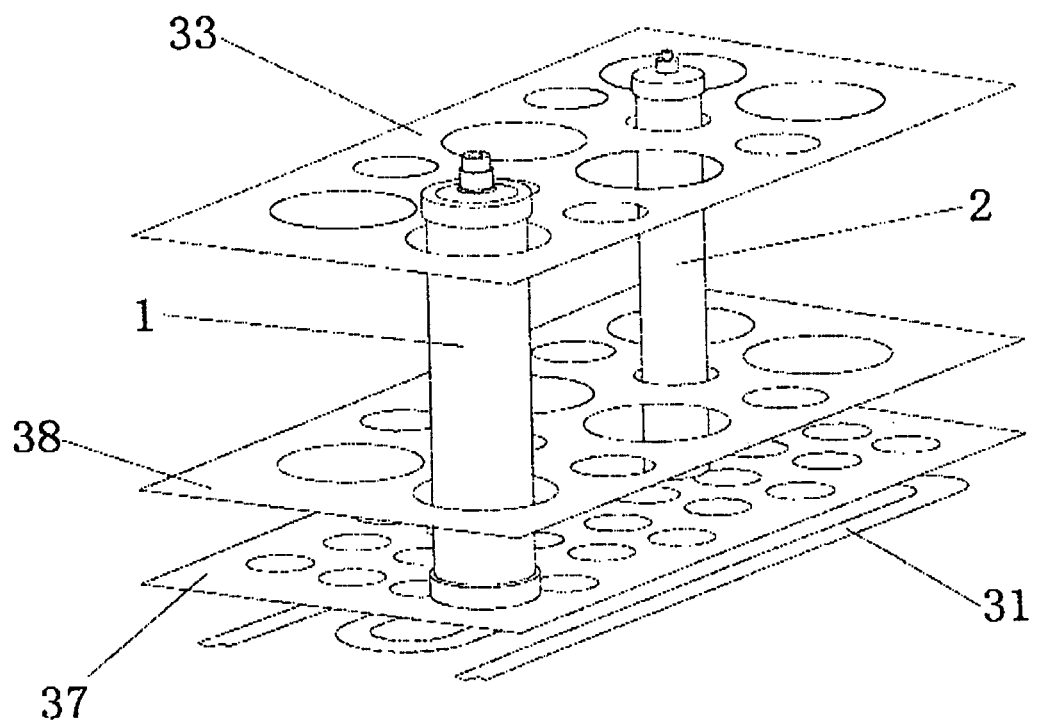
FIG. 3 is the schematic view of the usage status of the test box for the present adsorbed gas content measuring instrument.
Figure 4:
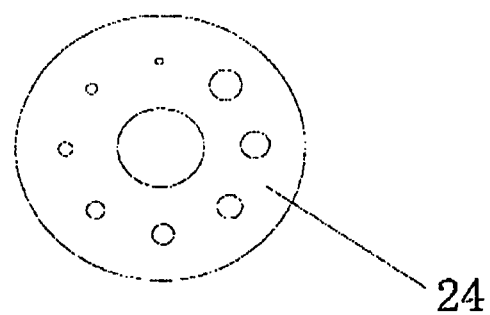
FIG. 4 is the schematic view of the interior structure of the test box for the present adsorbed gas content measuring instrument.

Preferably, the switching valve 23 can select a female buckle fit for the male buckle of the rapid connection of the valve port 14 so as to realize rapid and direct connection between the sealed cylinders and the gas collecting graduated canisters without a duct used, the canister body 21 is buckled with the seal 22, and the adjustment valve is composed of a restriction disk 24, an adjustment handwheel 25 and adjustment screws 26, wherein, the restriction disk 24 is located inside the seal 22, as shown in FIG. 2, and the restriction orifices are arranged with diameters increasing along circumference, for instance, 8 restriction holes with diameters being 1 mm, 1.5 mm, 2 mm, 2.5 mm, 3 mm, 3.5 mm, 4 mm and 4.5 mm can be set. The adjustment handwheel 25 is located outside the seal 22, through holes corresponding to the quantity and position of the restriction orifices are configured, and the diameters of the through holes are similar to those of the maximum restriction orifices; the position and size of the vent hole on the seal 22 is similar to that of a through hole on the adjustment handwheel 25; the restriction disk 24 and adjustment handwheel 25 are connected via the adjustment screws 26 and rotate synchronously. When rotating the adjustment handwheel 25 to make the through holes on the handwheel 25 and the restriction orifices on the restriction disk 24 coincide with the drain hole on the seal 22, the drain hole is opened, and the interior of the canister 21 is communicated with the outside.

Since the gas collecting graduated canister 2 of the present invention has good air tightness, in addition to the application of measuring the analyzed gas volume, it can be also used as a gas sample storage device for sampling after direct connection onto a gas component analyzer.

A heating element 31, a temperature controller 32 for monitoring the temperature inside the box and a top plate 33 are fixed in the test box 3; there are several through holes with the diameter corresponding to the outer diameter of the sealed cylinders 1 and gas collecting graduated canisters 2 on the top plate 33; the sealed cylinders 2 and gas collecting graduated canisters 3 are placed in the corresponding through holes; the heating element 31 and the temperature controller 32 are connected with the power interface 34 outside the box.

Preferably, the text box 3 further includes a cover 35, a drain valve 36, a partitioning plate 37 and an adhesion plate 38, wherein: the cover 35 is above the test box 3; the drain valve 36 is mounted at the bottom of the test box; the heating element 31 is fixed on the inner wall of the bottom of the box 3, the partitioning plate 37 is fixed above the heating element 31 and several through holes are set; holes corresponding to the top plate 33 are set on the adhesion plate 38 and removably installed in the middle of the test box 3.

The test box 3 of the present invention, featuring uniform heating and durable heat insulation, integrates constant water bath, test operating platform the container storage, placement, transit and carrying functions. With this box, the gas contained sample in the sealed cylinder 1 can be naturally analyzed in the original temperature condition of the ground bed, and has the merits of small volume, convenience for carrying and field application.

Furthermore, the gas collecting graduated canister 2 is required to be placed above the sealed cylinder 1 vertically with upside down, so a bracket 4 can further provided to support and stabilize the gas collecting graduated canister 2. Moreover, additional seal ring can be set on the connection of each part as desired to buffer the operation, prevent equipment damage and further improve the air tightness of the equipment.

The testing method for using the adsorbed gas content measuring instrument of the present invention mainly comprise seven steps from A to G:

Step A. Take out the sealed cylinders and the gas collecting graduated canisters.

Preferably, a measurement procedure is further included before testing after Step A: feed the saturated brine into the gas collecting graduated canisters, vertically place them with the seal downwards, adjust the adjustment valves, select the maximum opening size capable of preventing the brine from leaking as the opening size of the drain holes in Step E, afterwards, close the drain holes for next use. For example, rotate the adjustment handwheel to make the restriction orifices on the restriction disk from the minimum to a larger diameter coincide with the drain holes of the seal in sequence until the brine does not flow out, the restriction orifice at this time is selected as the drain hole diameter. After the gas collecting graduated canisters are communicated with the sealed cylinder, the drain hole is opened to the selected drain hole diameter.

The drain hole of the gas collecting graduated canister for the present invention adopts the principles of capillary force. With the drain hole diameter selected according to the above procedure, even the gas collecting graduated canister is placed with the seal downwards, the saturated brine does not flow out under the action of surface tension and the pressure outside and inside the drain hole is equal. Once gas enters into the gas collecting graduated canister, the brine in the canister body is forced out and the brine volume extruded is just equal to the collected gas volume.

Step B. Open the bottom cover of the sealed cylinder, introduce gas contained sample, fill up with saturated brine and then seal the cylinder. Feeding of the saturated brine may bring the air originally in the sealed cylinder out, and can prevent the analyzed gas from being dissolved in water to a maximum degree, thus the testing result is more accurate.

Step C. Feed water in the text box, turn the switch on, heat the water to the required temperature by means of the temperature controller and the heating element, and place the sealed cylinder into the text box vertically with the top cover upwards. At this time, the test box provides constant water bath environment required by the test for the sealed cylinder and the samples inside.

Step D. Fill the gas collecting graduated canister up with the saturated brine. Specifically, open a drain hole, feed saturated brine in the gas collecting graduated canisters by a duct with a male buckle on one end and a funnel on the other side, and then close the drain hole. Feeding saturated brine can fully remove the air in the gas collecting canisters. The gas collected afterwards will be analyzed gas, so the measuring result of the sample adsorbed gas content is more accurate. Preferably, put an appropriate amount of red colouring matter in the saturated brine, and then feed the resultant brine into the gas collecting graduated canister for the convenience of observation and metering.

Step E. Connect the sealed cylinder and the gas collecting graduated canister with the seal downwards, and open the drain holes of the gas collecting graduated canister. For instance, couple the female buckle of the switching valve 23 of the gas collecting graduated canister and the male buckle of the valve port 14 of the sealed cylinder to open the vent hole, open the drain hole according to the diameter selected by the measuring procedure before testing, then the gas naturally analyzed by the rock in the sealed cylinder 1 enters into the gas collecting graduated canister 2 under the action of buoyancy force, the brine in the gas collecting graduated canister 2 with the equivalent volume is discharged through the drain hole.

Step F. Record the liquid level of the gas collecting graduated canister regularly. The data recorded are the analyzed gas volume collected currently. It can be input into the computer processor to get the adsorbed gas content, analysis rate and other result during or after test.

Step G. After test, close the drain holes of the gas collecting graduated canister, and disconnect the connection it from the sealed cylinder. At this time, the switching valve 23 of the gas collecting graduated canister 2 is automatically closed, the gas sample can be kept in the canister body 21 without the need of transferring to other container. To collect the gas in the canister body 21, turn the switching valve 23 upwards, and connect it with a suitable male buckle for sampling.

After test, pour out the water in the test box, and then place the sealed cylinder and the gas collecting graduated canister with gas sample in the test box and then take the box.

The adsorbed gas content measuring instrument for the present invention is special for measuring the adsorbed gas content in the exploration and development of natural gas, especially for shale gas, coalbed methane and other unconventional natural gases. With this instrument, the resource potential and exploration prospect of the reservoir bed can be rapidly evaluated and researched, the gas-bearing property of different regions, the gas-bearing quantity layout rule and gas reservoir capacity of the reservoir bed can be researched. It can be also widely used in gas prevention detection and safety evaluation of mine, pedologic research, environmental protection and monitoring, surface chemistry, chemical industry and other fields. The instrument convenient for handling and carrying can be used for site test in the field, and can remove all possible interference factors, simple for operation and accurate for measuring result.

To sum up, the description above only shows the preferred embodiment of the present invention and shall not be considered as the limitation to the present invention in any form. The simple revisions, equivalent changes or modifications to the disclosed technical contents herein made by those skilled in this art are all within the protection scope of the present invention.

What is claimed is:

1. An adsorbed gas content measuring instrument comprising sealed cylinders, gas collecting graduated canisters and a test box, wherein:
    each sealed cylinder includes a cylinder body, a top cover fixedly connected with one end of the cylinder body, a bottom cover removably connected with the other end of the cylinder body and a valve port fixed on the top cover;
    each gas collecting graduated canister includes a sealed canister body, a seal with a drain hole and a vent hole, wherein the drain hole is provided with an adjustment valve, and the vent hole is equipped with a switching valve fit for the valve port of the sealed cylinder;
    a heating element, a temperature controller for monitoring the temperature inside the box and a top plate are fixed in the test box; there are several through holes with the outer diameter corresponding to the sealed cylinders and gas collecting graduated canisters on the top plate; the sealed cylinders and gas collecting graduated canisters are placed in the corresponding through holes; the heating element and the temperature controller are connected with a power interface outside the box.

2. The adsorbed gas content measuring instrument as claimed in claim 1, characterized in that the valve port of the sealed cylinder is the male end of a rapid connection coupling, the switching valve of the gas collecting graduated canister is the female end of the rapid connection coupling.

3. The adsorbed gas content measuring instrument as claimed in claim 1, characterized in that the adjustment valve of the gas collecting graduated canister is composed of a restriction disk, an adjustment handwheel and adjustment screws:
    wherein the restriction disk is located inside the seal, and restriction orifices are arranged with diameters increasing along the circumference of the restriction disk;
    the adjustment handwheel is located outside the seal, through holes corresponding to the quantity and position of the restriction orifices are configured, and the diameters of the through holes are similar to those of the maximum restriction orifice;
    the position and size of the vent hole on the seal of the gas collecting graduated canister is similar to that of a through hole on the adjustment handwheel;
    the restriction disk and adjustment handwheel are connected via the adjustment screws and rotate synchronously.

4. The adsorbed gas content measuring instrument as claimed in claim 1, characterized in that the middle part of the top cover of the sealed cylinder has a slope, between the middle part and the outer edge of the top cover and is an inclined surface.

5. The adsorbed gas content measuring instrument as claimed in claim 1, characterized in that a boss is set on the bottom cover of the cylinder towards one side of the interior of the cylinder.

6. The adsorbed gas content measuring instrument as claimed in claim 1, characterized in that the test box further includes a cover, a drain valve, partitioning plate and adhesion plate, wherein:
    the cover shall be above the test box;
    the drain valve is mounted at the bottom of the test box;
    the heating element is fixed on the inner wall of the box bottom, the partitioning plate is fixed above the heating element and contains several through holes;
    the adhesion plate is removably installed in the middle of the test box and contains through holes that correspond to those in the too plate.

7. The adsorbed gas content measuring instrument as claimed in claim 1, characterized in that the cylinder body of the sealed cylinder is coupled with the bottom cover.

8. The adsorbed gas content measuring instrument as claimed in claim 1, further comprising a bracket for supporting and stabilizing the gas collecting graduated canisters.

9. A testing method of the adsorbed gas content measuring instrument as claimed in any one of claim 1 to 8 comprising the following steps:
    A. take out the sealed cylinders and the gas collecting graduated canisters;
    B. open the bottom cover of the sealed cylinder, introduce the gas containing sample, fill up with saturated brine and then seal the cylinder;
    C. feed water into the test box, turn the instrument on, heat the water to the required temperature by means of the temperature controller and the heating element, and place the sealed cylinder into the test box vertically with the top cover upwards;
    D. fill the gas collecting graduated canister up with the saturated brine;
    E. connect the sealed cylinder and the gas collecting graduated canister with the seal downwards, and open the drain holes of the gas collecting graduated canister;
    F. record the liquid level of the gas collecting graduated canister regularly;
    G. after the test, close the drain holes of the gas collecting graduated canister, and disconnect the gas collecting graduated canister from the sealed cylinder.

10. The testing method as claimed in claim 9, characterized in that the following procedure is included after step A:
    feed the saturated brine into the gas collecting graduated canisters, vertically place them with the seal downwards, adjust the adjustment valves to select the maximum opening size capable of preventing the brine from leaking as the opening size of the drain holes in step E, and afterwards, close the drain holes for next use.

* * * * *